United States Patent [19]

Schmitz et al.

[11] 4,453,410
[45] Jun. 12, 1984

[54] METHOD AND APPARATUS FOR LOCATING MATERIAL DEFECTS IN HOLLOW BODIES

[75] Inventors: Hans-Peter Schmitz; Bernard Schleper, both of Oberhausen, Fed. Rep. of Germany

[73] Assignee: Ruhrchemie Aktiengesellschaft, Oberhausen, Fed. Rep. of Germany

[21] Appl. No.: 503,642

[22] Filed: Jun. 14, 1983

Related U.S. Application Data

[63] Continuation of Ser. No. 228,864, Jan. 27, 1981, abandoned.

[30] Foreign Application Priority Data

Jan. 31, 1980 [DE] Fed. Rep. of Germany ....... 3003349

[51] Int. Cl.³ ............................................. G01N 29/04
[52] U.S. Cl. ......................................... 73/640; 73/623
[58] Field of Search ................. 73/623, 622, 629, 637, 73/638, 639, 640

[56] References Cited

U.S. PATENT DOCUMENTS

| 3,121,324 | 2/1964 | Cowan | 73/623 |
| 3,417,609 | 12/1968 | Graham | 73/623 |
| 3,583,211 | 6/1971 | Brech et al. | 73/623 |
| 3,916,675 | 11/1975 | Perdijon | 73/622 |
| 4,174,636 | 11/1979 | Pagano | 73/639 |
| 4,269,066 | 5/1981 | Fischer | 73/639 |
| 4,388,831 | 6/1983 | Sherman | 73/623 |

OTHER PUBLICATIONS

"Testing Tube Welds from the Bore", *Ultrasonics*, pp. 208–210, Oct.–Dec. 1964.
J. Krautkramer et al., *Ultrasonic Testing of Materials*, pp. 456, 647, 648, Second Edition, 1977.
M. Robba et al., "Controlli Non Distruttivi di Fabricazion . . . ", *Metallurgia Italiana*, pp. 293–307, No. 4, 1968.
V. T. Pronyakin et al., "Ultrasonic Flaw Detection in Finned Tubes", *Defektoskopiya*, No. 1, pp. 16–19, Jan.–Feb. 1970, (Soviet Journal of Nondestructive Testing, 1970).
Engineering Index, Abstracts, p. 3187, vol. 71, 1968, Abstract of Article by M. Robba.

*Primary Examiner*—Stephen A. Kreitman
*Attorney, Agent, or Firm*—Jordan B. Bierman; Linda Bierman; C. Cornell Remsen, Jr.

[57] ABSTRACT

An ultrasonic probe is positioned within a hollow body such as a pipe for detecting possible flaws in the body wall. The probe is designed for rotational and longitudinal movement in said pipe and includes an ultrasonic transmitter/receiver mounted eccentrically within a liquid filled chamber of the probe, so that transmitted impulses strike the inner wall of the pipe at such an angle that the angle of refraction of the sound wave in the material of the wall is always less than 90°.

11 Claims, 4 Drawing Figures

FIG. 3
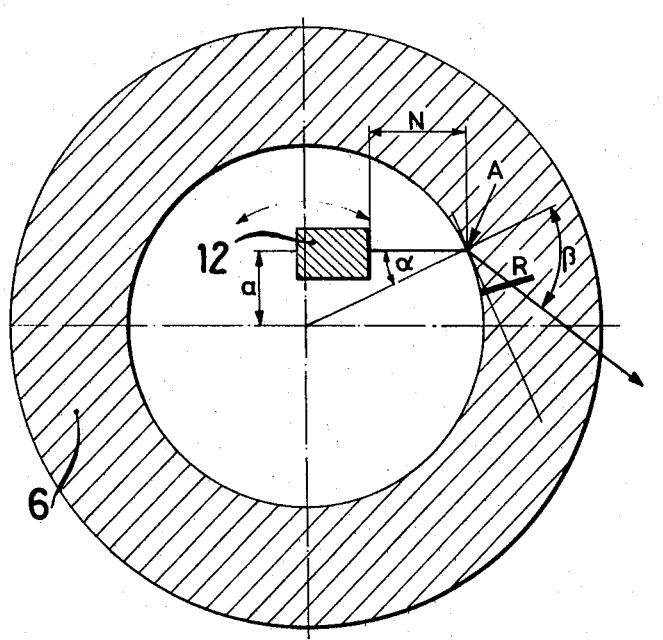
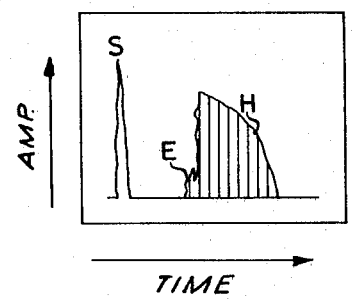
FIG. 4

METHOD AND APPARATUS FOR LOCATING MATERIAL DEFECTS IN HOLLOW BODIES

This application is a continuation of application Ser. No. 228,864, filed Jan. 27, 1981, now abandoned.

The present invention consists of a novel ultrasonic method for locating material defects in the walls of hollow bodies, as well as novel apparatus for carrying out such method. For this purpose, an ultrasonic transmitter/receiver is guided into the interior of the hollow body.

It is known that damage to thick-walled pipes can be detected with the aid of ultrasonics. Such checking procedure is carried out either from the outer surface inwardly, or from the inside outwardly using an ultrasonic probe which contains the transmitter and receiver and which is moved into the pipe.

The investigation of hollow bodies from the outside has the advantage that faults existing also in the interior of the wall can be clearly located. A disadvantage of this method however is that the outer surface of the hollow body must be directly accessible and not covered for example by insulation or other sheathing. External measurement procedures can thus be used only to a limited extent.

In order to obviate the aforementioned disadvantages, it has been proposed to carry out the examination of hollow bodies from the inside with the aid of a probe that is moved axially through the hollow body, and is simultaneously rotated. With this procedure, it is possible to detect the presence of faults in the wall of the hollow body, although it is not possible to locate them exactly. This defect in the test method is due to the fact that the rays reflected from the outer surface of the hollow body affect the accuracy of the test responses.

The need has therefore existed of developing a method that avoids the aforementioned difficulties, and enables defects on the surface and in the interior of the material to be detected and located in a simple manner.

The present invention accordingly includes a method for detecting material defects both on the surface and in the interior of the walls of hollow bodies with the aid of an ultrasonic probe guided through the hollow body.

The method is characterized in that the ultrasonic waves emitted by the probe head strike the inner surface of the hollow body at an angle of incidence $\alpha$ in a plane perpendicular to the hollow body axis such that the angle of refraction $\beta$ is preferably 60° to 80°.

The method according to the invention is based, like all test and measurement methods using ultrasonic waves, on receiving echoes formed by voids or spaces present in the interior of the material and on the surface.

The special feature of the new method is that the waves from the ultrasonic emitter do not fall vertically on the tangent drawn through the incidence point on the material surface, but strike at an angle $\alpha$. This angle is formed by the propagation direction of the wave and the perpendicular to the tangent at the incidence point of the wave on the surface. The angle should be chosen so that the angle of refraction $\beta$ of the sound wave in the material is always less than 90° and is in particular 60° to 80°. This ensures that in particular the ultrasonic waves incident on cracks are reflected so that they can be optimally received.

The required wave geometry is achieved by an eccentric arrangement of the ultrasonic probe head, which is arranged displaced with respect to a central arrangement by a specified linear distance parallel to the wave direction. The emitted ultrasonic waves are located in the plane perpendicular to the imaginary mid-axis of the hollow body. By concentrically rotating the ultrasonic probe by 360° about the mid-axis, the ultrasonic waves traverse the plane perpendicular to the mid-axis and thus enable a corresponding partial section of the hollow body to be checked.

The apparatus for carrying out the method according to the invention consists of an ultrasonic probe head which is located in a chamber filled with a coupling fluid and is connected to a feed drive arrangement. The probe is provided as well with an inlet for the coupling fluid and with a supply cable.

As an ultrasonic probe, there may be used, for example, a shock wave probe head of small dimensions which operates as transmitter and receiver in the megahertz range and whose dimensions are governed by the size of the hollow body. This probe head is arranged in a sealed chamber filled with coupling fluid. The coupling fluid serves to improve the transmission of the ultrasonic signals to the wall of the hollow body. Water or mineral oil is normally used as a coupling fluid.

In order to ensure as little coupling fluid as possible is lost, care must be taken to see that the chamber is reliably sealed. This is achieved by using for example cup seals or rubber O-rings.

However, any leakage losses that occur can be rectified by adding coupling fluid via a supply hose or pipe.

The use of a feed drive device, e.g. a universal joint linkage with an electrical or hydraulic drive system, means that the ultrasonic probe can be guided not only through straight pipe sections but can also be used in bent pipes. Appropriate feed drive systems are known and will not be described in detail. For investigating bent pipes, the feed drive system can be connected to a flexible shaft or to a universal joint linkage. Obviously, such linkages are not required when investigating straight pipes, and in this case a straight rod is sufficient.

Further details and features of the invention will be more fully described with reference to the accompanying drawings in which:

FIG. 3 is a theoretical transverse cross-sectional view illustrating the position of the ultrasonic transmitter/receiver relative to the inner wall of the hollow body to be examined, and FIG. 4 is an exemplary curve illustrating the type of test signals which may be received.

Figure 1:
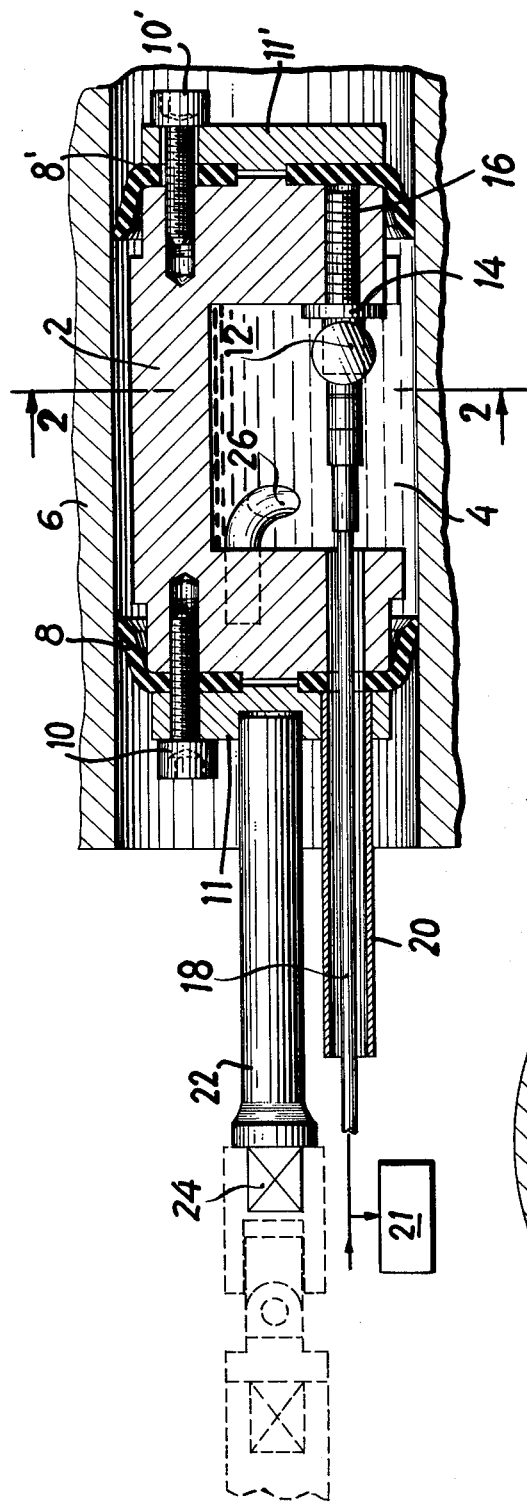
FIG. 1 is a longitudinal cross-sectional view showing an ultrasonic probe according to this invention, positioned within a hollow body to be examined.

As shown in detail in FIG. 1, the probe essentially comprises a cylindrical body portion 2 formed with a central hollow chamber 4 open at one side, and having an external diameter slightly smaller than the internal diameter of the hollow body 6, to be examined. The probe is slidably supported within the hollow body by end seals 8 and 8' attached to opposite ends of body portion 2 by means such as screws 10, 10' holding end plates 11, 11' respectively. The said end seals 8 and 8' not only support the probe within the hollow body but permit fluid to be contained within chamber 4 for purposes hereinafter described.

Positioned within chamber 4 is the probe head 12, preferably comprising any well-known piezo-electric transmitter/receiver for producing and receiving ultrasonic mechanical vibrations. It is supported in any suitable manner on plate 14 provided with threaded extension 16 screwed into body portion 2. Electrical connection to and from probe head 12 is provided by cable 18 protected in part by tube 20 attached in any suitable manner to the body portion 2. Ultrasonic waves received by probe head 12 can be converted in any known manner into displayed signals on luminescent screen or other device 21.

Fixedly attached in any suitable manner at one end to end plate 11 is a shank 22 preferably provided at its other end with means such as a Cardan joint 24.

The probe may be rotated within the hollow body to be explored by a hand crank or other means (not shown) acting through joint 24 and shank 22. Depending upon the length of the body to be explored, additional shaft lengths can be added end-to-end, as indicated in dotted lines in FIG. 1.

For testing purposes chamber 4 is preferably filled with a coupling fluid such as water or mineral oil to improve the transmission of the ultrasonic waves produced by the probe head 12 and the waves reflected from faults in the pipe to be tested. The coupling fluid may be supplied from any outside source through a hose or pipe (not shown) connected to inlet 26.

The mechanical operation of the probe can be readily understood. Through shank 22, Cardan joint 24 the probe can be both rotated within the hollow body to be examined directing the ultrasonic vibrations from probe 12 to various internal circumferential portions of the body, as shown in FIG. 2, and can be moved longitudinally within the body to test different cross-sectional areas.

The specific testing procedure in accordance with the present invention will now be described with reference to FIGS. 3 and 4.

Figure 2:
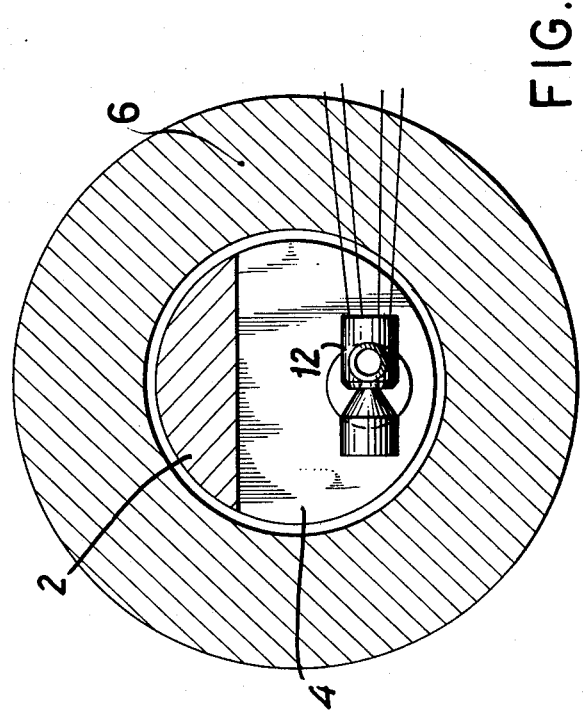
FIG. 2 is a transverse cross-sectional view along the line 2—2 of FIG. 1.

As will be seen in FIG. 2, and more specifically in FIG. 3, the ultrasonic probe head 12 is arranged eccentrically displaced from the pipe axis by the distance a. The generated ultrasonic pulses thus do not strike the inner wall of the hollow body radially, but at an angle of incidence $\alpha$, preferably approximately 30°, in order to ensure that the angle of reflection or refraction $\beta$ in the pipe material is as large as possible, i.e. is less than 90°, preferably 60°-80°. The greater $\beta$ is, the better the evaluation of the ultrasonic echoes for detecting material defects (size and location). It may be mentioned that the angle of incidence $\alpha$ is not a fixed value, but may be varied in accordance with the properties of the material being investigated.

The probe is rotated by 360° at a predetermined position in the hollow body, e.g. a pipe, and thus executes a concentric path about the pipe axis. When the ultrasonic pulses strike a material defect, the relfected ultrasonic pulses are converted into electrical signals (the strength of the reflected echoes is recorded as a function of the rotational movement of the ultrasonic probe), which is recorded for example on a display screen or recorder (21), in a manner known to the art.

The results of an exemplary test are illustrated by FIG. 4 as they might appear on such a screen or recorder 21, with the Y axis being a measure of amplitude and the X axis a measure of time. In such case, S would be the transmitted signal and E the signal normally reflected from the inner wall of the pipe. In the case of a crack such as R, FIG. 3, an envelope curve such as H may be produced. The falling away of the envelope curve means that no echoes are received from the defect site in the wall material, and it may therefore be concluded that the ultrasonic probe in this position no longer detects the defect site with its correspondingly refracted sound waves in the pipe wall medium. The reflected pulses that are received by the ultrasonic probe follow the same path as the emitted pulses. In this way and from the intensity of the reflected echoes, the position and extent of the fault site can be established.

The near field length N is predetermined by the design of the ultrasonic probe, where N corresponds to the focusing of the emitted ultrasonic pulses. Depending on the dimensions of the pipe being investigated, the use of a suitably designed ultrasonic probe is recommended, since the near field length N should correspond to the distance from the ultrasonic probe outlet to the point of incidence A.

As previously described, ultrasonic probe is guided axially into the pipe and then checks the next pipe section, corresponding to its then present position, after being rotated by 360° about the pipe axis. This procedure is repeated as often as necessary until each pipe section has been completely checked.

This new test equipment is suitable for investigating pipes of widely differing materials, e.g. of iron, chrome-nickel steels, ceramics, and plastics materials such as polyethylene.

Obvious variations will occur to those skilled in this art. The manner of mounting the ultrasonic transmitter/receiver within the chamber of the device is only illustrative, only the positioning of this device relative to the axis of the probe being critical. The probe can be rotated and axially moved within the pipe by any convenient apparatus in addition to that shown and described. Accordingly the invention is not limited except as set forth in the claims which follow.

We claim:

1. The method of detecting defects in the material of hollow bodies which includes the steps of generating, transmitting and receiving ultrasonic waves within the hollow body from and to a point eccentrically positioned within the hollow body with the path of said waves extending directly and unimpededly between said point and said hollow body at right angles to but not radially from the longitudinal axis of said hollow body, the distance along said path corresponding to the focusing of the transmitted ultrasonic waves in accordance with the dimensions of the hollow body to be tested, rotating said path concentrically about an axis parallel to the longitudinal axis of the hollow body and transferring the waves reflected and received from said hollow body into detectable signals indicative of the presence or absence of defects in the material of the hollow body.

2. Method according to claim 1 in which the transmitted ultrasonic waves strike the inner surface of said hollow body at an angle formed by the direct path of the emitted wave and the perpendicular to the tangent at the point of incidence such that the angle of refraction in the medium of the wall of the hollow body as formed by the refracted wave and the perpendicular to the tangent at said incidence point is less than 90°.

3. Method according to claim 2 in which said angle of refraction is 60° to 80°.

4. Apparatus for detecting flaws in hollow bodies, comprising a probe body having an outer circumference smaller than the inner circumference of the hollow body to be examined and provided with a central hollowed-out portion open at one side, sealing rings attached to each end of said probe body supporting the latter within the hollow body and forming a chamber with said hollowed-out portion, means generating, transmitting and receiving ultrasonic waves, means mounting said last means within said chamber so as to radiate and receive waves along an unimpeded path extending directly between said last means and the inner surface of the hollow body to be tested, said direct unimpeded path extending for a distance corresponding to the focusing of the transmitted ultrasonic pulses, and means rotating said probe body within said hollow body along a concentric path about the longitudinal axis of the hollow body and moving the same axially through the latter.

5. Apparatus according to claim 4 in which said generating, transmitting and receiving means is so mounted within said chamber that the direct path of the unimpeded transmitted waves strikes the inner surface of said hollow body at an angle formed by the emitted wave and the perpendicular to the tangent at the point of incidence such that the angle of refraction in the medium of the wall of the hollow body as formed by the refracted wave and the perpendicular to the tangent at said incidence point is less than 90°.

6. Apparatus according to claim 4 in which said generating, transmitting and receiving means is so mounted within said chamber that the direct unimpeded path of the transmitted waves strikes the inner surface of said hollow body at an angle formed by the emitted wave and the perpendicular to the tangent at the point of incidence such that the angle of refraction in the medium of the wall of the hollow body as formed by the refracted wave and the perpendicular to the tangent at said incidence point is 60° to 80°.

7. Apparatus according to claim 4 in combination with means supplying lubricating fluid to said chamber and about said generating, transmitting and receiving means.

8. Apparatus according to claim 7 in which said generating, transmitting and receiving means is so mounted within said chamber that the direct unimpeded path of the transmitted waves strikes the inner surface of said hollow body at an angle formed by the emitted wave and the perpendicular to the tangent at the point of incidence such that the angle of refraction in the medium of the wall of the hollow body as formed by the refracted wave and the perpendicular to the tangent at said incidence point is less than 90°.

9. Apparatus according to claim 7 in which said generating, transmitting and receiving means is so mounted within said chamber that the direct unimpeded path of the transmitted waves strikes the inner surface of said hollow body at an angle formed by the emitted wave and the perpendicular to the tangent at the point of incidence such that the angle of refraction in the medium of the wall of the hollow body as formed by the refracted wave and the perpendicular to the tangent at said incidence point is 60° to 80°.

10. Apparatus for detecting flaws in hollow bodies, comprising a probe body having an outer circumference smaller than the inner circumference of the hollow body to be examined and provided with a central hollow-out portion open at one side, sealing rings attached to each end of said probe body supporting the latter within the hollow body and forming a chamber with said hollowed-out portion, means generating, transmitting and receiving ultrasonic waves, means mounting said last means within said chamber so as to radiate and receive waves along an unimpeded path extending directly between said last means and the inner surface of the hollow body to be tested, said direct, unimpeded path extending in a direction so that the transmitted ultrasonic waves hit the inner wall of said hollow body to provide an angle of refraction with the material thereof of less than 90°, and for a distance corresponding to the focusing of the transmitted ultrasonic waves, and means rotating said probe body within said hollow body along a concentric path about the longitudinal axis of the hollow body, and moving the same axially through the latter.

11. Apparatus for detecting flaws in hollow bodies, comprising a probe body having an outer circumference smaller than the inner circumference of the hollow body to be examined and provided with a central cut-out portion open at one side, said cut-out portion forming with the inner wall of said hollow body a chamber in said probe body, means generating, transmitting and receiving ultrasonic waves, means mounting said last means within said chamber so as to radiate and receive waves along an unimpeded path extending directly between said last means and the inner surface of the hollow body to be tested, said direct unimpeded path extending for a distance corresponding to the focusing of the transmitted ultrasonic pulses and striking the inner surface of said hollow body at an angle formed by the emitted wave and the perpendicular to the tangent at the point of incidence such that the angle of refraction in the medium of the wall of the hollow body as formed by the refracted wave and the perpendicular to the tangent at said incidence point is 60° to 80°, and means rotating said probe body within said hollow body along a concentric path about the longitudinal axis of the hollow body and moving the same axially through the latter.

* * * * *